United States Patent [19]

Nagasaki

[11] Patent Number: 5,014,711
[45] Date of Patent: May 14, 1991

[54] ULTRASONIC DIAGNOSIS APPARATUS

[75] Inventor: Tatsuo Nagasaki, Musashino, Japan

[73] Assignee: Olympus Optical Co., Ltd., Tokyo, Japan

[21] Appl. No.: 475,790

[22] Filed: Jan. 30, 1990

Related U.S. Application Data

[62] Division of Ser. No. 155,843, Feb. 12, 1988, Pat. No. 4,945,915.

[30] Foreign Application Priority Data

Feb. 20, 1987 [JP] Japan .................................. 62-36931
Apr. 3, 1987 [JP] Japan .................................. 62-82628

[51] Int. Cl.$^5$ .............................................. A61B 8/00
[52] U.S. Cl. .................................. 128/660.07; 73/644
[58] Field of Search .................... 128/660.09, 660.10; 73/625–626, 642, 644

[56] References Cited

U.S. PATENT DOCUMENTS

| | | | |
|---|---|---|---|
| 3,911,730 | 10/1975 | Niklas | 73/624 |
| 4,112,411 | 9/1978 | Alais | 367/135 |
| 4,131,024 | 12/1978 | Mezrich et al. | 73/606 |
| 4,457,175 | 7/1984 | Ramsey et al. | 73/606 |
| 4,570,488 | 2/1986 | Miwa et al. | 73/626 |
| 4,671,293 | 6/1987 | Shaulov | 128/661.01 |

FOREIGN PATENT DOCUMENTS 2579761 10/1986 France .
2053475A 2/1981 United Kingdom .
2075797A 11/1981 United Kingdom .

*Primary Examiner*—Francis Jaworski
*Attorney, Agent, or Firm*—Frishauf, Holtz, Goodman & Woodward

[57] ABSTRACT

An ultrasonic diagnosis apparatus comprises a probe for transmitting an ultrasonic beam onto a target body and receiving an ultrasonic echo from the target body and a diagnosis device for supplying a transmission pulse to the probe and processing an electrical signal from the probe to prepare tomographic image information. The probe includes a transmitter, which transmits an ultrasonic beam on each line of a slice of the target body from an oblique direction so as to sequentially irradiate the ultrasonic beam on the individual pixels of the slice, an ultrasonic image pick-up element, which has electric-/acoustic transducer elements provided in parallel to the slice and arranged two-dimensionally with respect to each pixel of the slice and converts an ultrasonic echo into an electrical signal in accordance with sound pressure, an ultrasonic lens provided in parallel to the slice to converge the ultrasonic echo from each pixel of the slice on an associated electric/acoustic transducer element of the ultrasonic image pick-up element, a transmission multiplexer for sequentially scanning a line on which the ultrasonic beam from the transmitter is to be irradiated, and a reception multiplexer, coupled to the individual electric/acoustic transducer elements of the ultrasonic image pick-up element so as to two-dimensionally scan these converting elements.

5 Claims, 10 Drawing Sheets

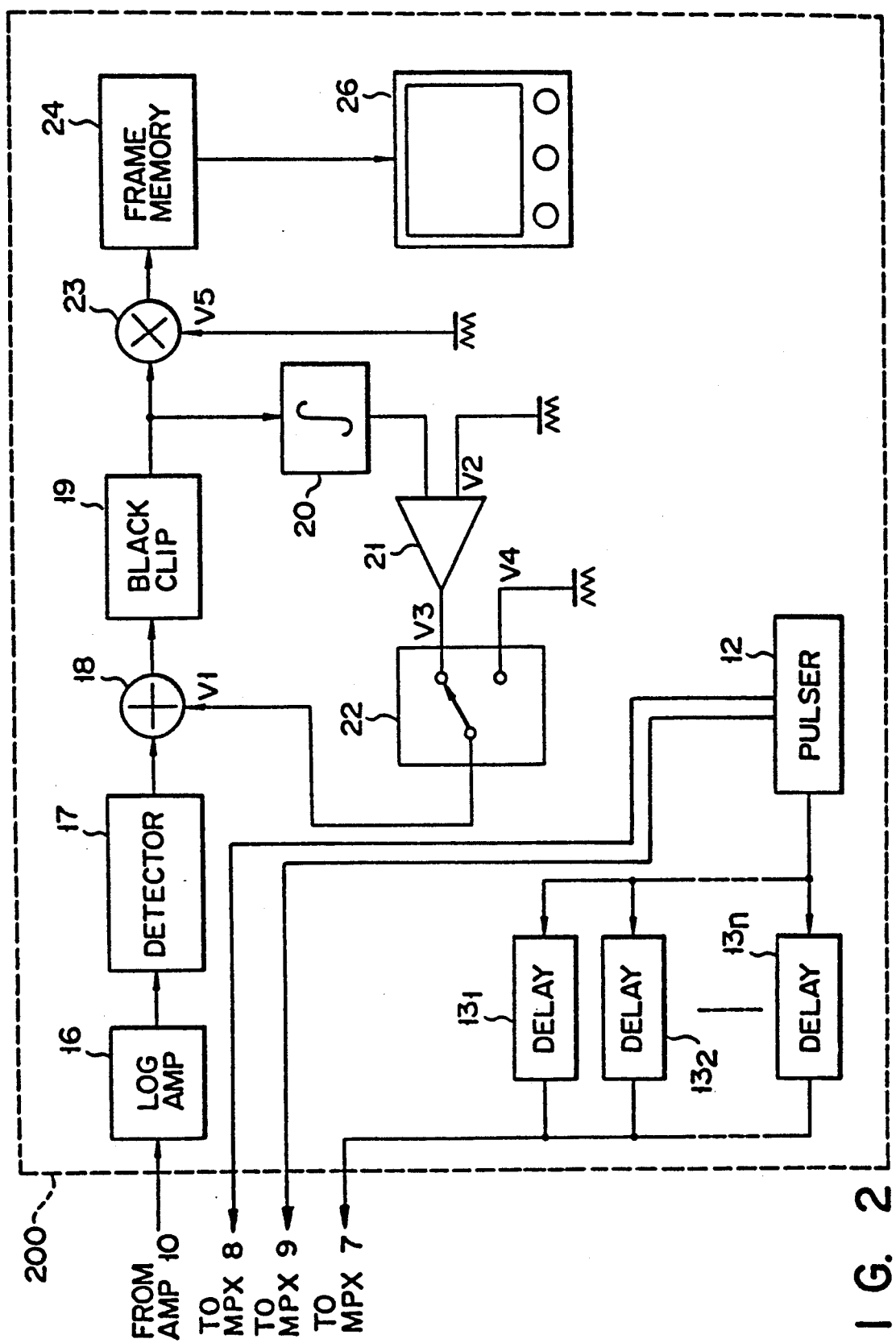
F I G. 2

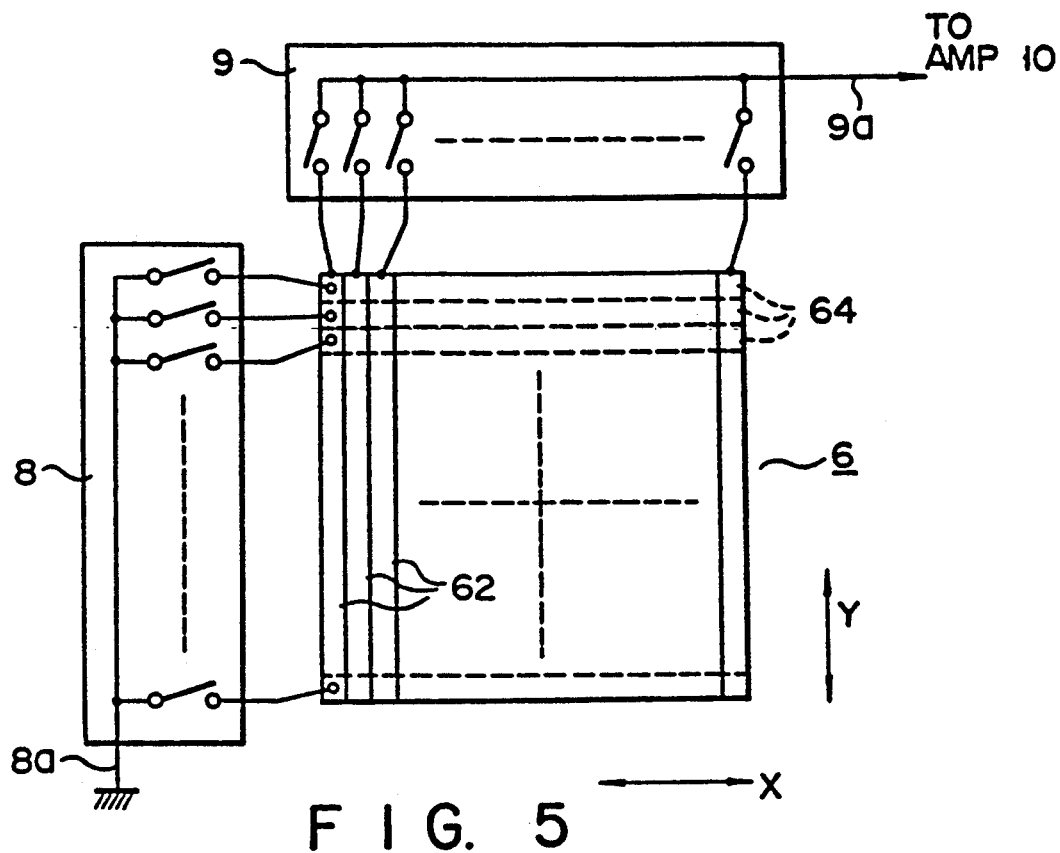
F I G. 5
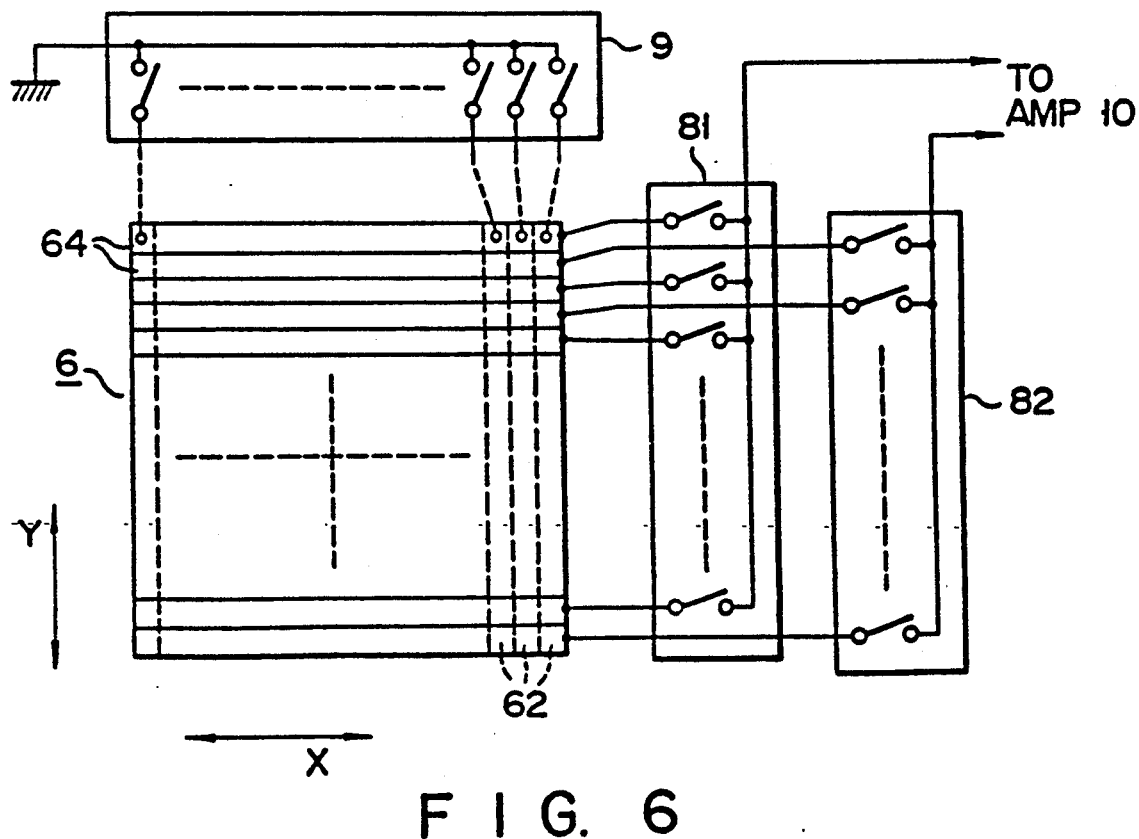
F I G. 6

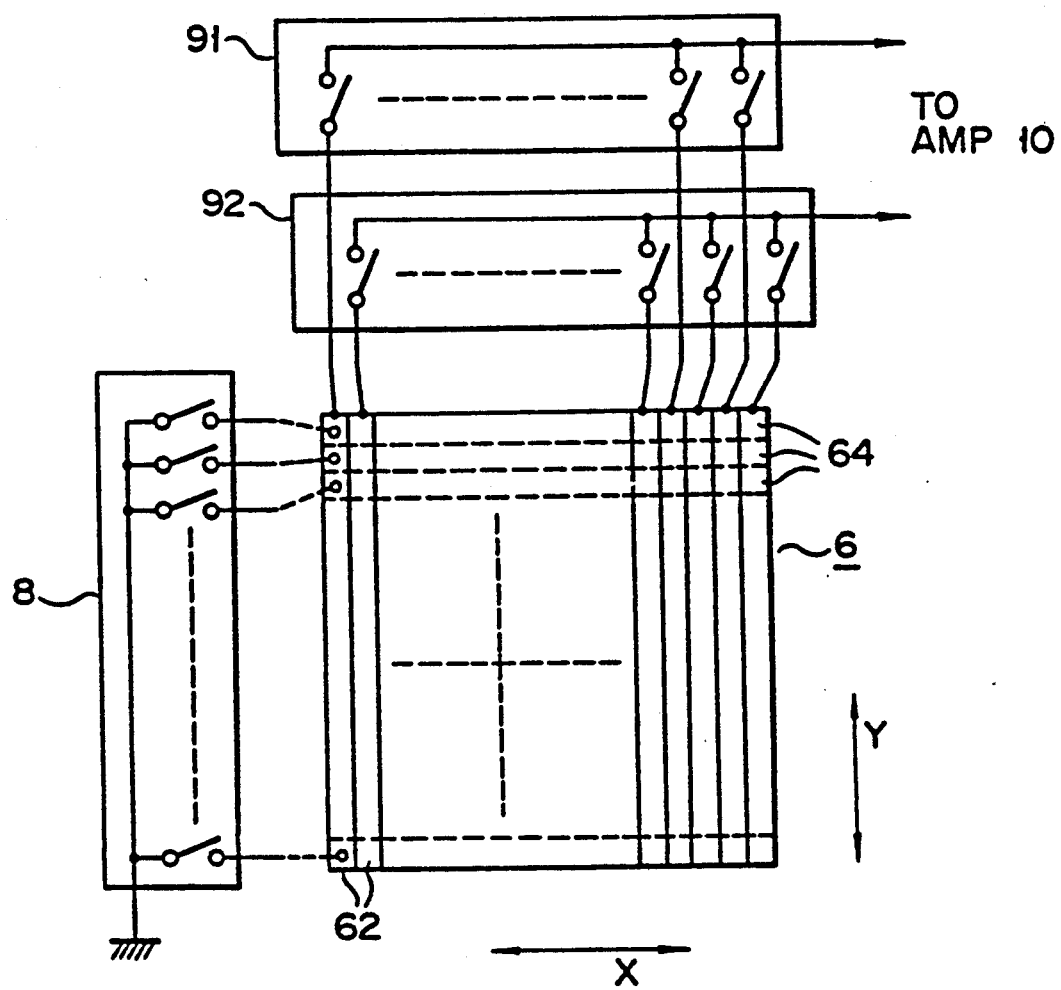
F I G. 7

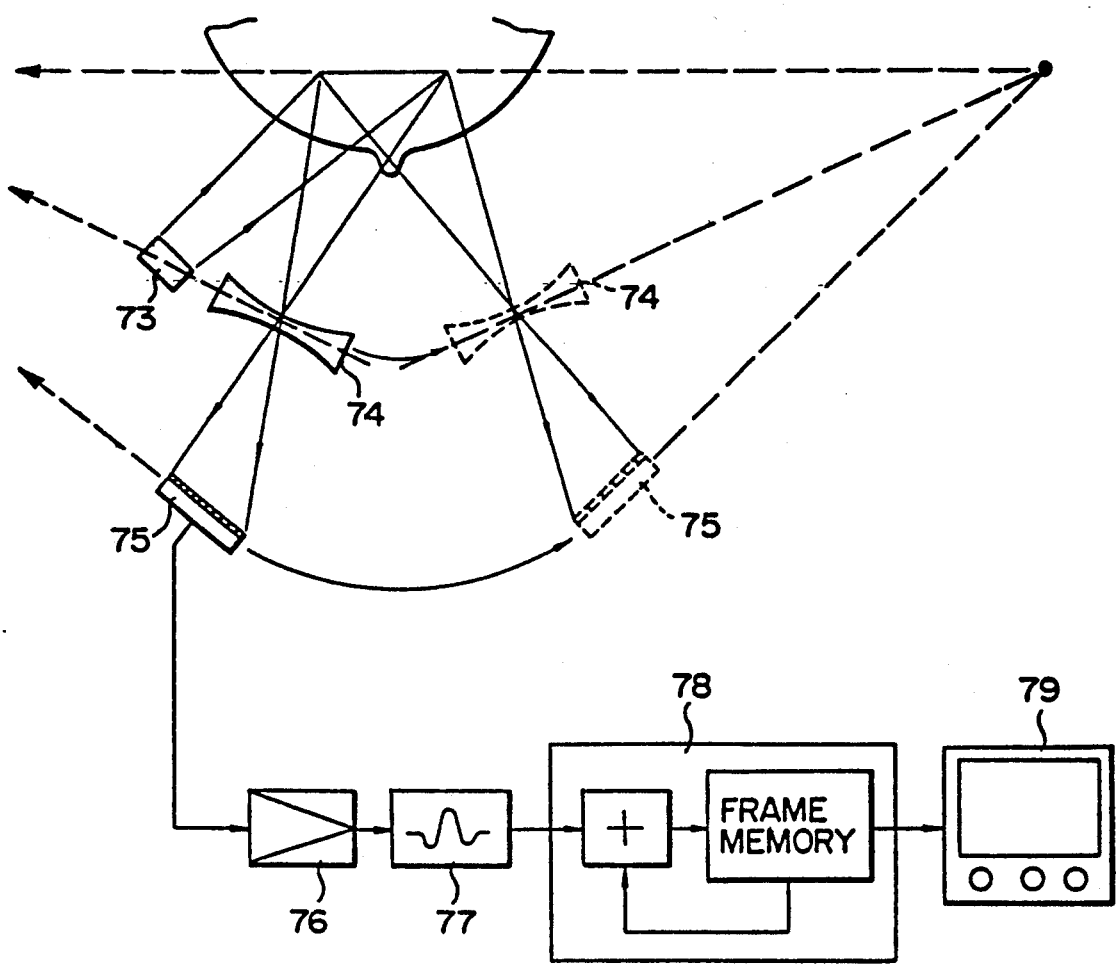
F I G. 8
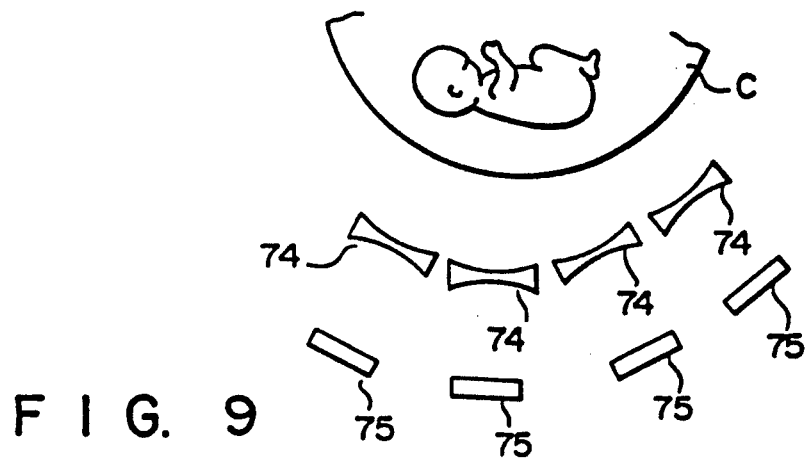
F I G. 9

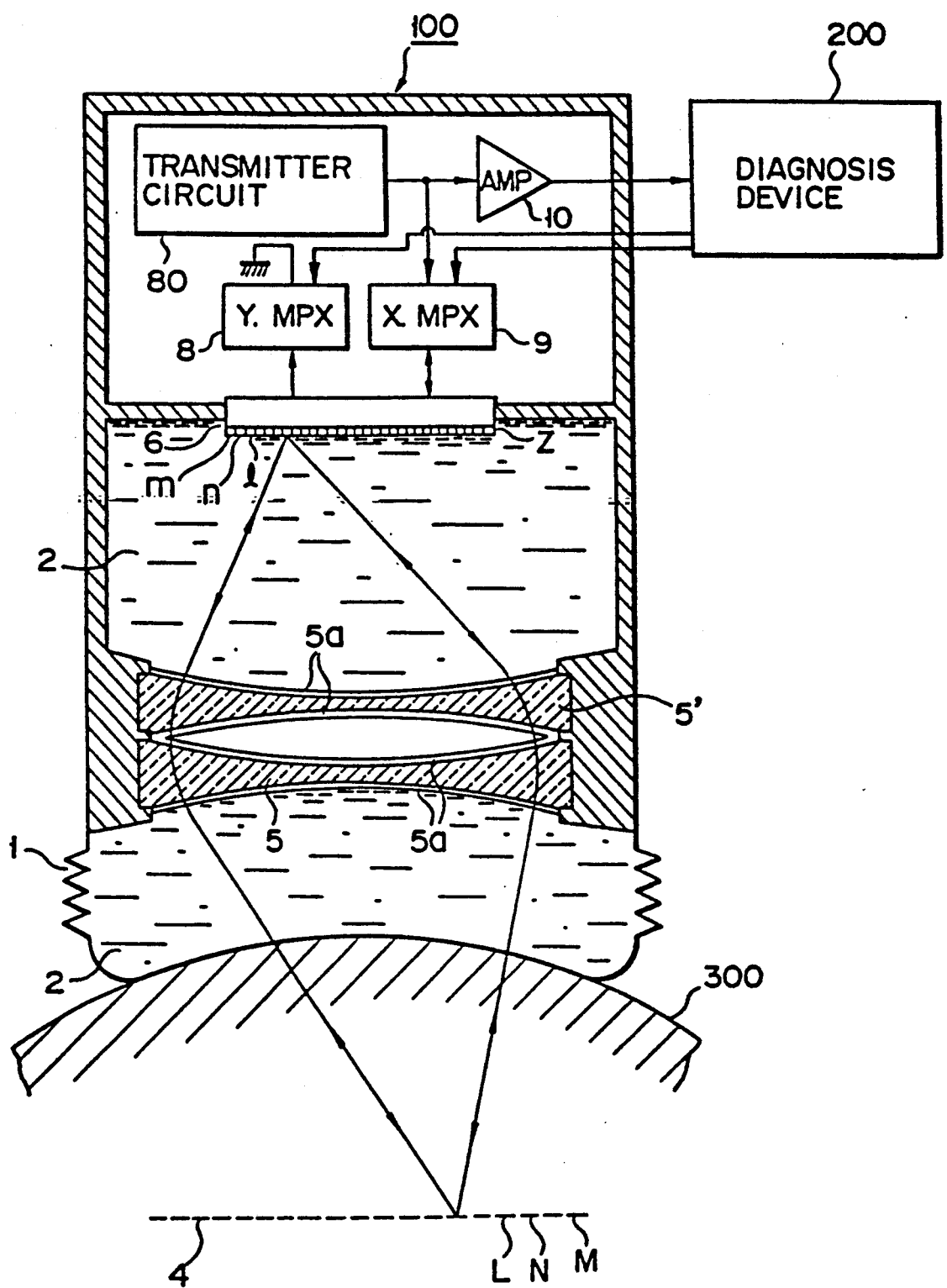
F I G. 10

ULTRASONIC DIAGNOSIS APPARATUS

This application is a division of Ser. No. 155,843 filed Feb. 12, 1988, and now U.S. Pat. No. 4,945,915.

BACKGROUND OF THE INVENTION

1. Field of the Invention

The present invention relates to an ultrasonic diagnosis apparatus which irradiates an ultrasonic pulse onto a target body under examination, receives an echo pulse from the target body and displays a tomographic image of the body, and in particular, to an improvement of an ultrasonic pulse transmission/ reception system.

2. Description of related art

Conventional major apparatuses for displaying a tomographic image of a target body using ultrasonic pulses are B-mode ultrasonic diagnosis apparatuses as disclosed in "Ultrasonic Pulse Technical Handbook," p 810-813, from Nikkan Kogyo or "Ultrasonic Diagnosis," p 81-84, from Igaku Shoin.

B-mode ultrasonic diagnosis apparatuses are capable of displaying a tomographic image of a sliced section of a target body along the advancing direction of an ultrasonic beam. More specifically, these apparatuses perform a single irradiation of an ultrasonic beam so as to acquire an image for a single scanning line along the advancing direction of the ultrasonic wave, and then perform linear scanning in or sector scanning the irradiating direction of the ultrasonic beam, thereby providing a tomographic image for one screen.

Since ultrasonic pulses generally have a property of gradual diversion with their propagation, the cross-section of each ultrasonic pulse does not become smaller than the size of a probe. For this property, therefore, the B-mode apparatuses have a low azimuth resolution (the resolution in the direction perpendicular to the advancing direction of an ultrasonic beam).

If the tip of the probe is designed to have a recessed surface, the ultrasonic beam would once converge at or near its focal point before it diverges. This ensures that a beam attained is narrower at the proximity of the focal point than the aperture of a transducer, thus improving the azimuth resolution at that region. This method, however, narrows the focusing range (the range within which the diameter of the ultrasonic beam is smaller than a predetermined value) in the depth direction (the advancing direction of the ultrasonic beam), and hence is not practical.

To cope with this problem, therefore, there has been a system in actual use, which uses a transducer with a small aperture for transmission/reception of an ultrasonic wave in such a way as to provide a nearly constant convergence (azimuth resolution) with respect to a certain depth from the skin of the target body and a relatively larger focusing range.

Although the transducer with a small aperture has an advantage of reducing the beam convergence so as to increase the focusing range, it certainly has a disadvantage that the azimuth resolution is deteriorated.

As an alternative, C-mode apparatuses have been proposed, which acquire a number of B-mode tomographic images at given intervals to construct a three-dimensional image, and extracts, from the acquired image, only those pieces of image information which are for the same depth of the target body (preferably, near the focal point) to reconstruct a tomographic image of the target slice along the direction perpendicular to the advancing direction of the ultrasonic beam. This, however, requires a number of B-mode images to acquire a single C-mode image, which is time-consuming and is not practical in actual use in the case where a target slice is in motion.

SUMMARY OF THE INVENTION

Accordingly, it is an object of this invention to provide an ultrasonic diagnosis apparatus that can significantly improve the azimuth resolution.

An ultrasonic diagnosis apparatus according to this invention comprises an ultrasonic transmitting element for irradiating an ultrasonic beam on a single slice of a target body from a direction other than a direction parallel to the slice to sequentially scan individual points of the slice with the ultrasonic beam, and an ultrasonic image pick-up element for sequentially receiving an ultrasonic echo reflected from the individual points of the slice to acquire an image indicating an ultrasonic characteristic of the slice.

BRIEF DESCRIPTION OF THE DRAWINGS

FIG. 2 is a block diagram of the main body of the ultrasonic diagnosis apparatus;

FIG. 5 is a diagram illustrating a circuit for reading out a signal from the ultrasonic image pick-up element;

FIG. 6 is a diagram illustrating a first modification of the signal readout circuit shown in FIG. 5;

FIG. 7 is a diagram illustrating a second modification of the signal readout circuit shown in FIG. 5;

FIG. 8 is a diagram illustrating a first modification of the first embodiment of this invention;

FIG. 9 is a diagram illustrating a second modification of the first embodiment of this invention;

FIG. 10 is a block diagram of an ultrasonic diagnosis apparatus according to a second embodiment of this invention;

DETAILED DESCRIPTION OF THE PREFERRED EMBODIMENT

Figure 1:
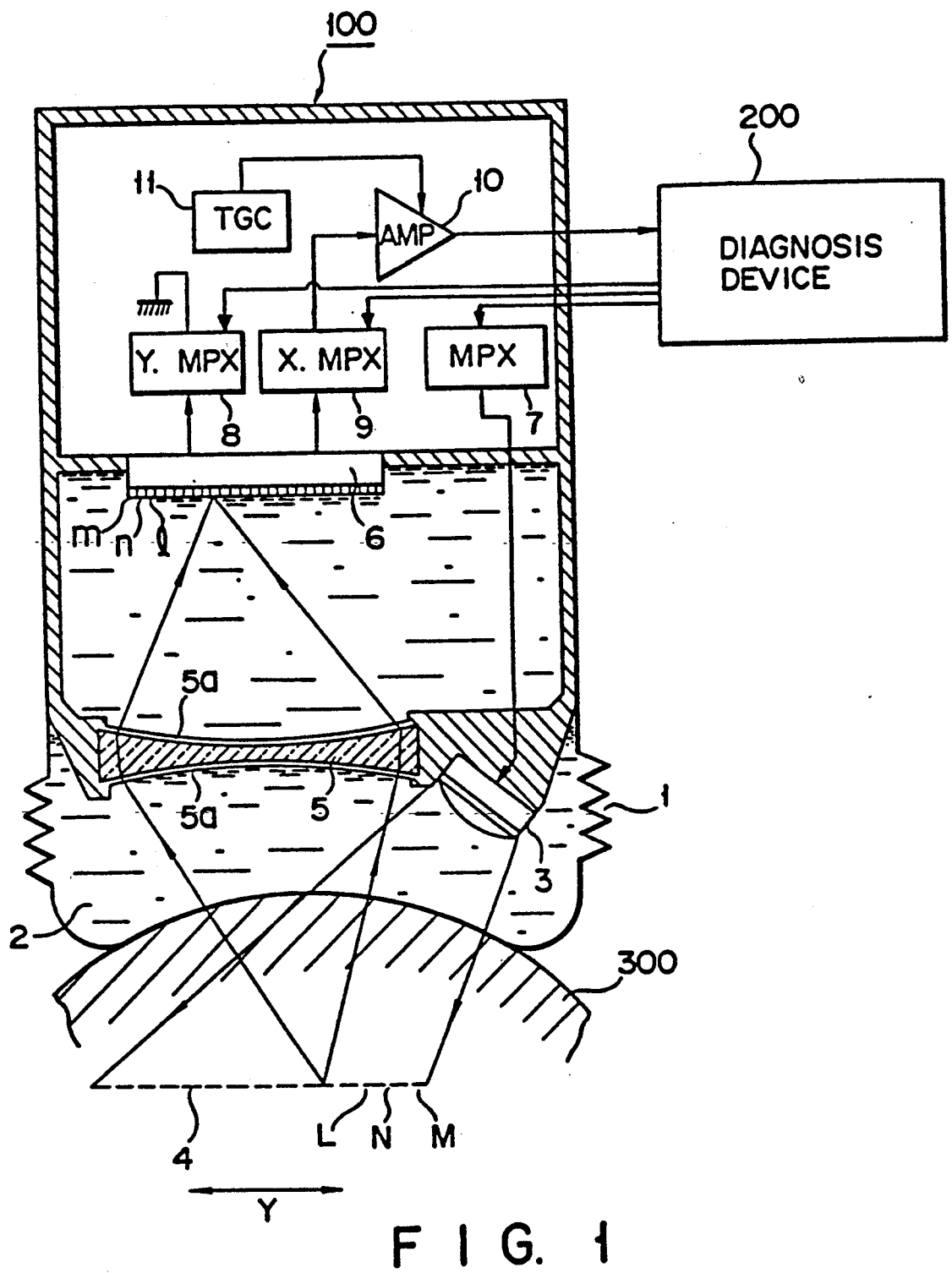
FIG. 1 is a block diagram of an ultrasonic diagnosis apparatus according to a first embodiment of this invention.

As shown in FIG. 1, the ultrasonic diagnosis apparatus according to the first embodiment of this invention comprises a probe 100 and a diagnosis device 200. In the figure, numeral "300" is a target body. At the tip portion of probe 100 that faces target body 300 is a bellows 1 mounted surrounding the tip portion to make the tip portion of the probe to stably contact the surface of target body 300. Inside bellows 1 is a sound absorber disposed to prevent irregular reflection of an ultrasonic beam. Bellows 1 further includes an acoustic medium 2, such as water, sealed therein. Since the sound speed in water varies with the temperature thereof, probe 100 is equipped with a temperature control mechanism for keeping the temperature constant and a bubble removing mechanism, though not shown.

An ultrasonic transmitter 3 is mounted on the tip portion of probe 100. This transmitter 3 comprises a linear array transducer arranged in the direction perpendicular to the face of FIG. 1, and irradiates an ultrasonic beam obliquely with respect to a desired or target slice 4 whose tomographic image is to be acquired. The present apparatus differs in the beam transmitting direction from conventional B-mode apparatuses which irradiate an ultrasonic beam in parallel to slice 4 (actually, within the slice surface).

At the center of the tip portion of probe 100 is an ultrasonic lens 5 with a large angular aperture, arranged approximately in parallel to slice 4. Lens 5 converges an ultrasonic echo from target body 300 and forms an ultrasonic image of slice 4 onto the surface of ultrasonic image pick-up element 6, which is provided in the probe approximately in parallel to lens 5. Lens 5 is made of a material which is similar to acoustic medium 2 in terms of acoustic impedance but differs from it in sound speed. When acoustic medium 2 is water, lens 5 is made of a plastic material such as acrylic resin. When a plastic material is used, an aspherical lens can be easily made. The diameter of lens 5 is about 60 to 70 mm. Lens 5 has an acoustic matching layer 5a coated on either side thereof. This lens 5 may either be a single lens or a combined lens, and may further be provided with an aberration eliminating mechanism or a zoom or focus adjustment mechanism for varying the vertical position of slice 4 to be displayed.

The position of slice 4 is determined primarily based on the focal distance of lens 5. The depth of slice 4 can arbitrarily be defined by varying the distance between lens 5 and target body 300 by stretching or compressing bellows 1. Since the sound speed in water as acoustic medium 2 is considered to be nearly equal to that in target body 300, there is no echo at the boundary between the water and target body 300.

Probe 100 is divided into two sections, namely, the front section and the rear section. Ultrasonic image pick-up element 6 is provided in the front section in which acoustic medium 2 is also sealed. The image pick-up element 6 converts the sound pressure distribution of an ultrasonic beam received at its image pick-up surface, into a sequence of electrical signals (tomographic signals).

Inside the rear section of probe 100 is a multiplexer 7 provided to select the linear array transducers of transmitter 3. Multiplexers 8 (Y direction) and 9 (X direction) are for sequentially reading out the electrical signals from image pick-up element 6. Multiplexer 9 has its output connection terminal coupled to a pre-amplifier 10, and multiplexer 8 has its output connection terminal grounded. A tomographic signal for each scanning line output from multiplexer 9 is amplified in pre-amplifier 10 whose amplification increases with time under the control of a time gain controller TGC 11 while a signal for a single scanning line is being read out.

Diagnosis device 200 comprises, as shown in FIG. 2, a pulser 12 whose output (transmission pulse) is supplied to multiplexer 7 through a plurality of delay lines $13_1$, $13_2$, ..., $13_n$ having different delay times. Multiplexer 7 then selectively supplies transmission pulses from delay lines $13_1$, $13_2$, ... $13_n$, to n transducers. Multiplexers 8 and 9 are also controlled by diagnosis device 200, via pulser 12 or the like therein.

The output of pre-amplifier 10 is supplied to a frame memory 24 through a logarithmic amplifier 16, an amplitude detector 17, an adder 18, a black clip circuit 19 and a multiplier 23. The output of black clip circuit 19 is supplied to the adder 18 through an integrator 20, a comparator 21 and a selector 22. The output of frame memory 24 is displayed on a monitor 26.

Figure 3:
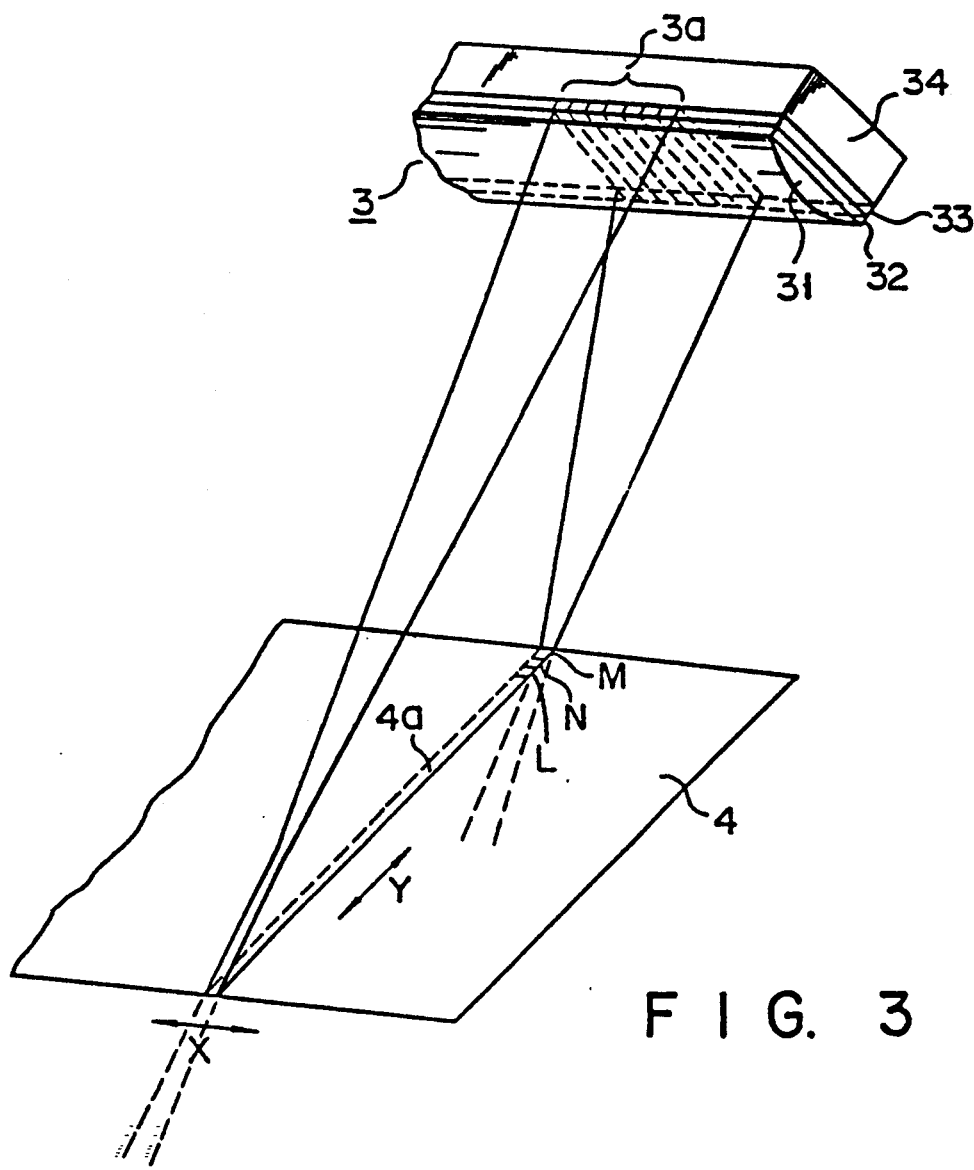
FIG. 3 is a diagram for explaining the principle of scanning one line on a slice with an ultrasonic beam.

FIG. 3 illustrates transmitter 3 in detail. The transmitter 3 comprises an acoustic lens 31, an acoustic matching layer 32, an electric/acoustic transducing element 33 and a damper member 34 securely adhered together, in order to irradiate an ultrasonic beam with a uniform intensity distribution in the Y direction on slice 4. Transmitter 3 (electric/acoustic transducing element 33) has a number of transducer rows arranged in the X direction also included in slice 4 and perpendicular to the Y direction.

When a transducer group 3a comprising n transducers is selected by multiplexer 7 and the individual transducers are supplied with transmission pulses that have passed through delay lines $13_1$ to $13_n$, the ultrasonic pulses from the transducers are irradiated with the respective delays. If the delays for delay lines $13_1$ to $13_n$ are determined such that delay line $13_{n/2}$ has the greatest delay with the delays for the other delay lines being smaller toward delay line $13_1$ or $13_n$, the ultrasonic pulses irradiated from the individual transducers converge in the X direction so that the pulses are irradiated on a single scanning line 4a in a superimposed manner. If the ultrasonic beam is irradiated obliquely with respect to the target slice, the irradiation of the beam may be uniform with respect to the slice in the X direction; however, the beam is converged on a single line in order to suppress a ghost echo caused by irregular reflection or multi-reflection of the beam.

Since the beam transmitting direction of transmitter 3 is oblique with respect to slice 4 (line 4a), the ultrasonic beam is irradiated on line 4a from the closest point to transmitter 3 to the farthest. That is, the irradiation is carried out first on point M and then on points N, L, and so forth. In this manner, one line 4a of slice 4 is scanned.

Echoes from points M, N, L, ... on line 4a of slice 4 are converged by lens 5 with their respective delays on points m, n, 1, ... on a single line on pick-up element 6 corresponding to line 4a.

Figure 4:
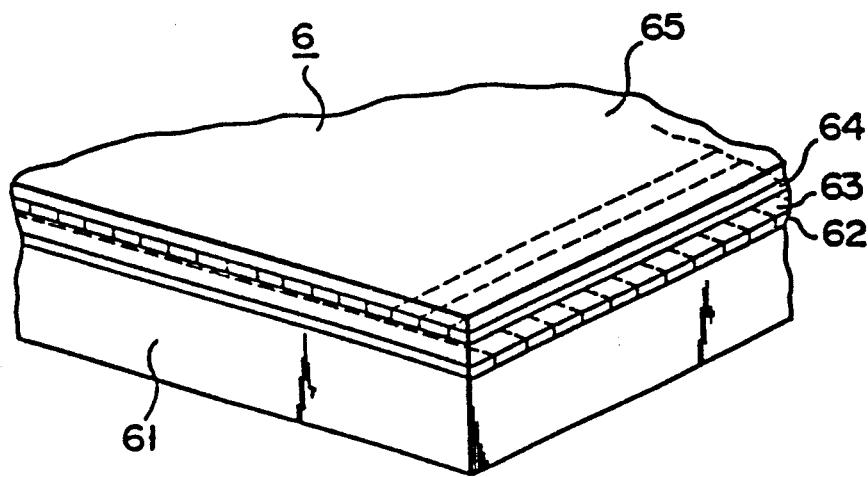
FIG. 4 is a diagram illustrating the cross section of an ultrasonic image pick-up element.

FIG. 4 illustrates the cross-sectional structure of image pick-up element 6. On an element-mounting table or substrate 61 serving as an acoustic damper are a signal electrode 62, an electric/acoustic transducer element 63, a ground electrode 64 and an acoustic matching layer 65 fixed together in a laminated structure. The acoustic matching layer 65 faces in the direction from which an ultrasonic beam comes. Signal electrode 62 and ground electrode 64 are each divided into a plurality of segments, their divisional directions being opposite to each other. The cross point between segments corresponds to one pixel. A material such as PVDF or $PVF_2$ that has smaller sound coupling in the lateral direction, is advantageous for electric/acoustic transducer element 63 because that the element 63 can be subjected to pixel division simply by dividing the electrodes 62 and 64. In contrast, PTZ if used for electric/acoustic transducer-element 63 requires a mechanical cutting of element 63 in addition to the dividing of the electrodes.

FIG. 5 illustrates the structure of a circuit for reading out an electrical signal from image pick-up element 6. Signal electrode 62 is divided into a plurality of segments in the X direction (see FIG. 3), each segment extending in the Y direction. Ground electrode 64 is divided into segments in the Y direction, each of which extends in the X direction. Each segment of signal electrode 62 is coupled to multiplexer 9, while each segment of ground electrode 64 is coupled to multiplexer 8. Multiplexer 8 has its common electrode 8a grounded, and multiplexer 9 has its common electrode 9a coupled to pre-amplifier 10.

Since the ultrasonic beam is irradiated obliquely as described earlier, an image signal for one scanning line can be extracted pixel by pixel by switching multiplexer 8 in accordance with the times (about 200 ns intervals) needed for the ultrasonic pulses to travel from ultrasonic transmitter 3 to points m, n, l, ... of image pick-up element 6 after being reflected at the respective points M, N, L, .... An image signal for the next one scanning line can be extracted pixel by pixel by switching transducer groups by multiplexer 7 to move (scan) the line to be irradiated with an ultrasonic beam in the Y direction and at the same time switching the detection line of the image pick-up element by multiplexer 9. In this manner, the image signal of a desired slice of the target body can be scanned two-dimensionally by switching multiplexers 8 and 9.

According to this embodiment, the target slice can be scanned with an ultrasonic beam by obliquely irradiating the beam on the individual scanning lines of the slice and the echo is converged on the image pick-up element using the ultrasonic lens so as to convert the sound pressure of the echo into an electrical signal for each pixel, thereby providing an ultrasonic tomographic image. As compared with the conventional B-mode apparatuses, the present apparatus can provide an ultrasonic tomographic image with improved azimuth resolution.

The resolution of the image pick-up element is determined in the target slice by the angular aperture of lens 5 and the frequency of the ultrasonic pulse as follows.

$$2.44 \, F/D\lambda$$

where F is the focal distance of lens 5, D is the diameter of the lens and $\lambda$ is the wavelength of the pulse.

The resolution in the direction perpendicular to the slice is proportional to the pulse width multiplied by $1/\sin \theta$ where $\theta$ is the irradiation angle of the ultrasonic pulse on the slice.

To be more specific, the resolution in the X direction is proportional to the converging distribution of lens 5 in the azimuth direction multiplied by the directivity of the transmission pulse. In this respect, transducer 3 irradiates an ultrasonic beam converged on one line. The resolution in the Y direction is proportional to the converging distribution of lens 5 in the azimuth direction multiplied by the envelope waveform of the pulse and $1/\cos \theta$. The resolution in the direction perpendicular to the slice is proportional to the envelope waveform multiplied by $1/\sin \theta$ and the converging distribution of lens 5 in the axial direction.

The azimuth resolution attained from the above equations in this embodiment is about 7 times greater than what is attained by the conventional apparatuses.

The following explains how to process a received signal.

Pre-amplifier 10, which has a good noise factor, amplifies the received signal to a sufficiently high level to prevent deterioration of the S/N ratio in a later stage circuit. Since echoes from points M and N, even on the same line, travel different distances, the attenuation in the target body varies in accordance with the traveled distances if the gain is set constant. This causes variation in the sensitivity. In this respect, therefore, the variation is compensated in time gain controller 11; that is, the amplification is gradually increased during the reception time for the individual lines.

Logarithmic amplifier 16 subjects the input signal to a logarithmic-amplification in accordance with the dynamic range (about 60 dB) of the ultrasonic echo.

Detector 17 detects the amplitude of the ultrasonic echo to provide an image signal.

Adder 18 adds this image signal and a gain control voltage V1 from selector 22, and black clip circuit 19 clips a voltage below 0 V.

The gain control voltage V1 can be attained as follows. The output of black clip circuit 19 is integrated in integrator 20 to provide the mean value of the image signal for one frame. This mean value is compared with an automatic gain setting voltage V2 by comparator 21 and the attained difference is also amplified there. The output (automatic gain control voltage) V3 of comparator 21 and a manual gain control voltage V4 are switched by selector 22 so that one of them is used as the gain control voltage V1.

The image signal put through the above gain control process is multiplied, in multiplier 23, by a dynamic range control voltage V5 for controlling the display range, and the resultant signal is written in frame memory 24. Frame memory 24 converts the image signal into a signal having a frequency corresponding to the scanning frequency for the standard television system and adds a sync. signal to the converted signal. The output of frame memory 24 is displayed on TV monitor 26.

The following explains modifications of the system for reading signals from the image pick-up element according to the first embodiment. The signal readout circuit in the first embodiments described above performs the signal readout for each line; however, the first modification of the first embodiment performs the signal readout for two lines simultaneously. The first modification, as shown in FIG. 6, has Y-direction multiplexer 8 formed in a double structure and has two multiplexers 81 and 82 coupled to every other ground electrode 64, respectively. As opposed to the first embodiment, the common terminal of multiplexer 9 is grounded and the common terminals of multiplexers 81 and 82 are coupled to apparatus body 200 through pre-amplifier 10. Consequently, the circuit arrangement from pre-amplifier 10 to multiplier 23 has a double structure.

This first modification is particularly effective in an ultrasonic diagnosis apparatus utilizing a chirp wave, as disclosed in U.S. patent application Ser. No. 107,497 entitled "Pulse Compression Apparatus For Ultrasonic Image Processing", now U.S. Pat. No. 4,788,981, issued Dec. 6, 1977. Since the chirp wave has a long duration, the image pick-up time can be reduced by simultaneously reading image signals for two lines.

The double structure requires that linear array transducer 3 irradiates an ultrasonic beam proper for simultaneously scanning two lines. Therefore, it is necessary to vary the delay times of delay lines $13_1$ to $13_n$ to reduce the convergence of the ultrasonic beam in the X direction.

According to the second modification shown in FIG. 7, X-direction multiplexer 9 is designed to have a double structure so that two multiplexers 91 and 92 are coupled to every other signal electrode 62, respectively. The common terminals of multiplexers 91 and 92 are coupled to apparatus body 20 through pre-amplifier 10. Like the first modification, the second modification also has a double-structured circuit arrangement between pre-amplifier 10 and multiplier 23.

The second modification can shorten the switching speed of multiplexers 91 and 92 to $\frac{1}{2}$.

Modifications of the first embodiment will now be explained. Since ultrasonic beams are coherent, it is likely to cause a speckle pattern. The use of a transmission ultrasonic beam in pulse form as is done in the first embodiment can reduce the speckle pattern significantly, but cannot eliminate it completely. FIG. 8 illustrates the first modification of the first embodiment which can completely eliminate the speckle pattern and which can further improve the resolution. In FIG. 8, numeral 73 is an ultrasonic transmitter, 74 is an ultrasonic lens and 75 is an image pick-up element. Upon completion of image pick-up for one screen, ultrasonic lens 74 and image pick-up element 75 are moved in the arrow direction, and this operation is repeated many times. Lens 74 and image pick-up element 75, after being shifted to a different position, are positioned so as to be able to pick up an image of the same slice.

The information of a plurality of thus attained tomographic images is amplified by an amplifier 76 and is supplied through an enhancer 77 to an accumulator 78 which comprises a frame memory and an adder, to attain an averaged value. Consequently, the speckle pattern can be eliminated. Enhancer 77 is provided for correcting the "blurring" that is caused by the accumulation performed by accumulator 78.

This modification can therefore remove the speckle pattern and improve the resolution as well as the S/N ratio. The movement of ultrasonic lens 74 and image pick-up element 75 may be two-dimensional as well as one dimensional, in order to increase the number of image pick-up operations. As an alternative to actually move lens 74 and image pick-up element 75, a plurality of ultrasonic lens 74 and image pick-up elements 75 may be provided as shown in FIG. 9 so that these components can be switched to produce the same effect as the former modification.

A second embodiment of this invention will be explained below with reference to the block diagram of FIG. 10. The second embodiment differs from the first embodiment in two points. The first difference is that ultrasonic transmitter 3 is not provided but ultrasonic image pick-up element 6 serves as a transmitter as well as a receiver. The second difference is that a transmission circuit 80 (corresponding to pulser 12 and delay circuit 13 of the first embodiment) is provided in probe 100 and the output of this circuit 80 is supplied through multiplexer 9 to image pick-up element 6. Lens 5 is illustrated as a combination of two lenses 5 and 5' here.

Figure 11:
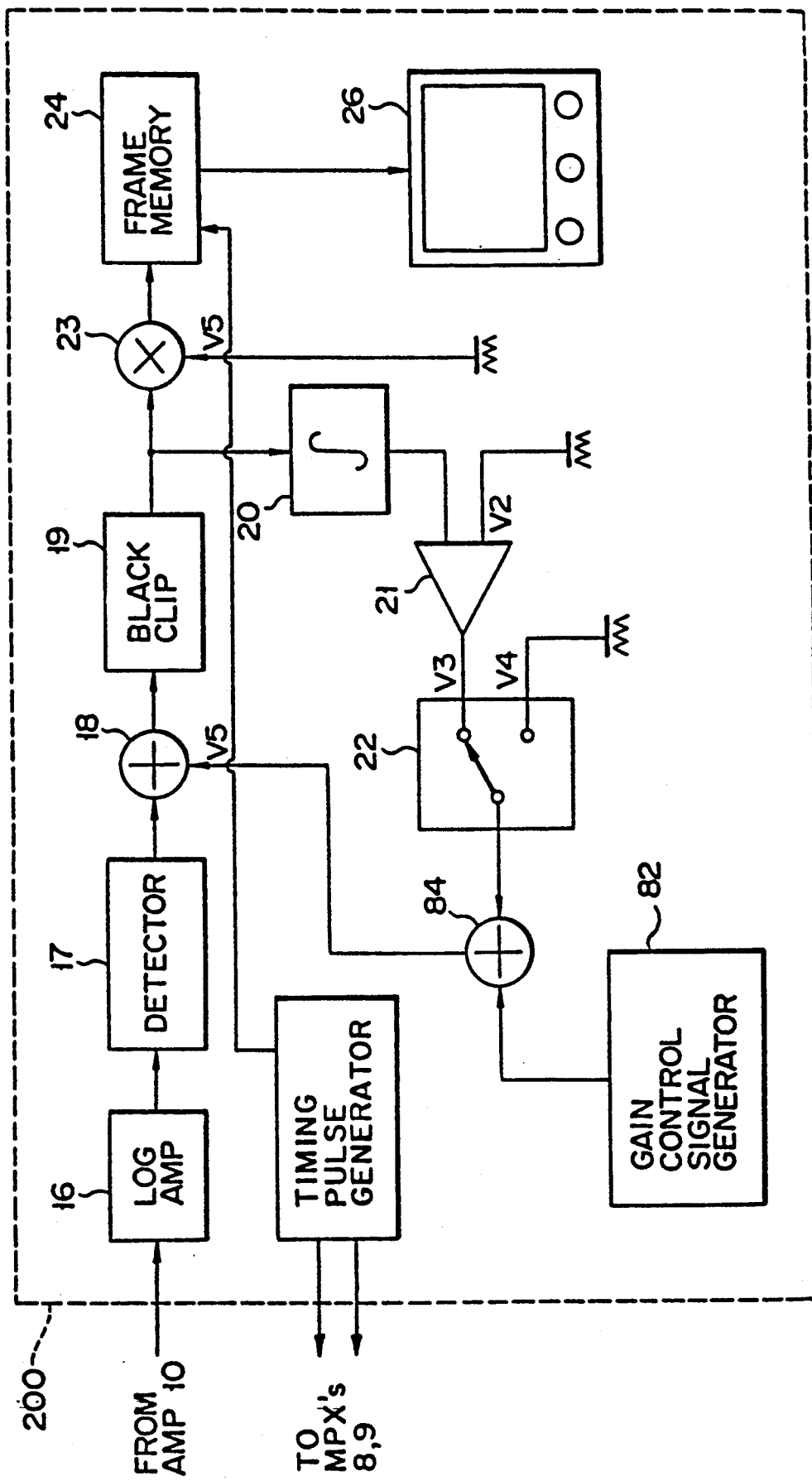
FIG. 11 is a block diagram of the main body of the ultrasonic diagnosis apparatus according to the second embodiment.

FIG. 11 illustrates the detailed structure of diagnosis device 200. Diagnosis device 200 is the corresponding device of the first embodiment further provided with two-dimensional gain control signal generator 82. The output of the gain control signal generator 82 is added with the output of selector 22 in adder 84, whose output is supplied to adder 18 as a gain control signal.

Figure 12:
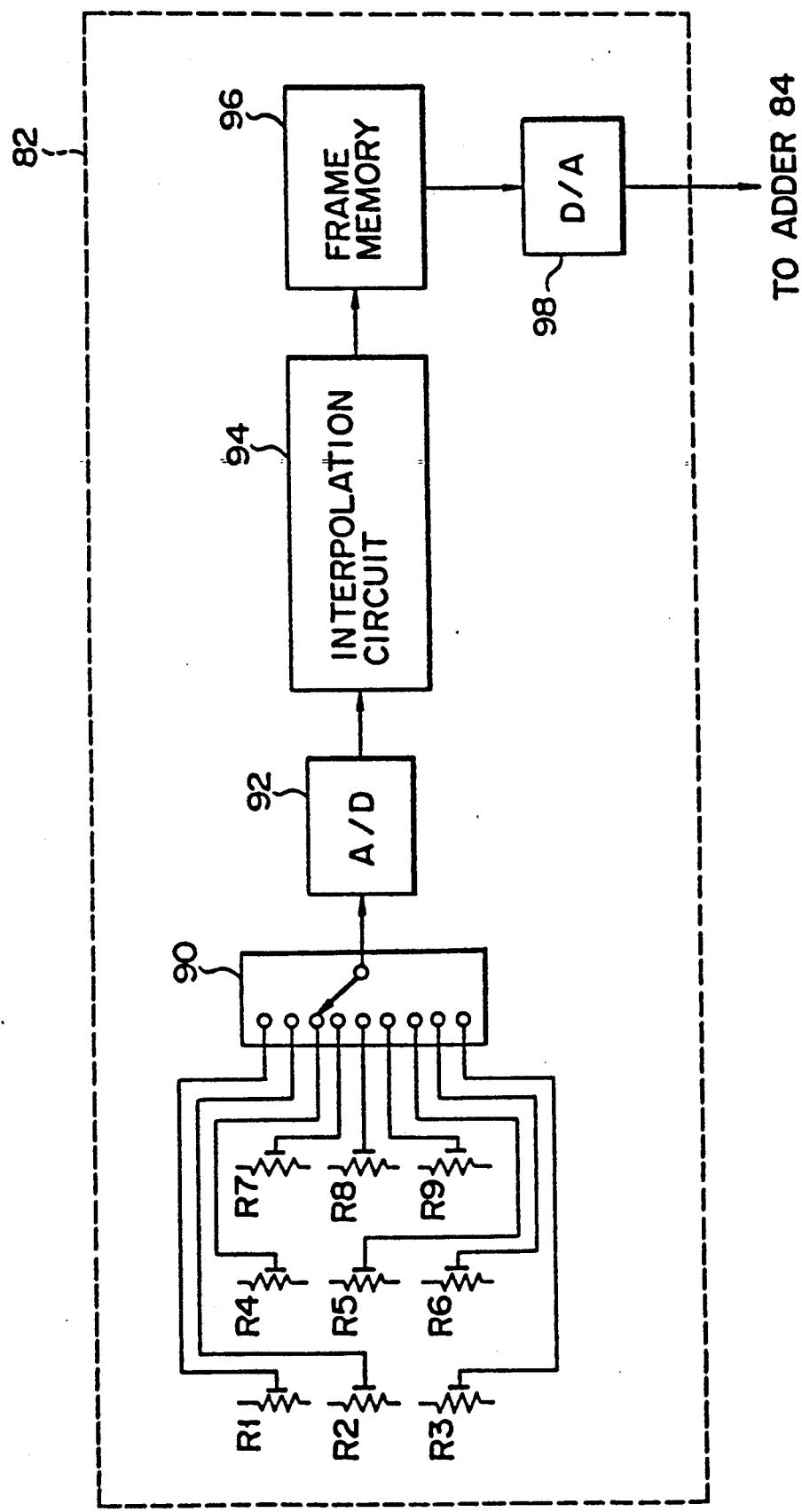
FIG. 12 is a block diagram of a gain control signal generator shown in FIG. 11.

FIG. 12 illustrates gain control signal generator 82 in detail. R1 to R9 are resistors arranged in two dimensions on an operation panel on the top surface of diagnosis device 200, and their resistances are adjusted in accordance with the desired gains of corresponding positions on the screen (top right, top center, etc.) One of resistors R1–R9 is selected by a multiplexer 90 and is supplied through an A/D converter 92 to an interpolation circuit 94, which interpolates nine resistances per screen to attain the resistance for each pixel of the image pick-up element and writes the resultant data into a frame memory 96. That is, frame memory 96 stores the resistance for determining the gain for each pixel of the image pick-up element. The output of frame memory 96 is supplied through a D/A converter 98 to adder 84.

The other section has the same structure as the corresponding section of the first embodiment.

In the second embodiment, multiplexers 8 and 9 are coupled to ultrasonic image pick-up element 6 as per the first embodiment. Multiplexer 9 selects one signal electrode segment 62 of image pick-up element 6, and multiplexer 8 sequentially selects pixels m, n, l, ... on signal electrode segment 62 and supplies a transmission signal through multiplexer 9 to the selected signal electrode segment 62. Consequently, ultrasonic pulses are sequentially transmitted from pixels m, n, l, ... on the signal electrode segment 62.

The transmitted ultrasonic beams are reflected at corresponding points M, N, L, ... of slice 4 and received by the pixels m, n, l, ... of image pick-up element 6. Therefore, if pixels m, n, l, ... of one signal electrode segment 62 of image pick-up element 6 are again sequentially selected after the beams from the pixels m, n, l, ... have been reflected at points M, N, L, ... and have returned to the original pixels m, n, l, ..., the image signal for each pixel is input to diagnosis device 200 through pre-amplifier 10.

Figure 13:
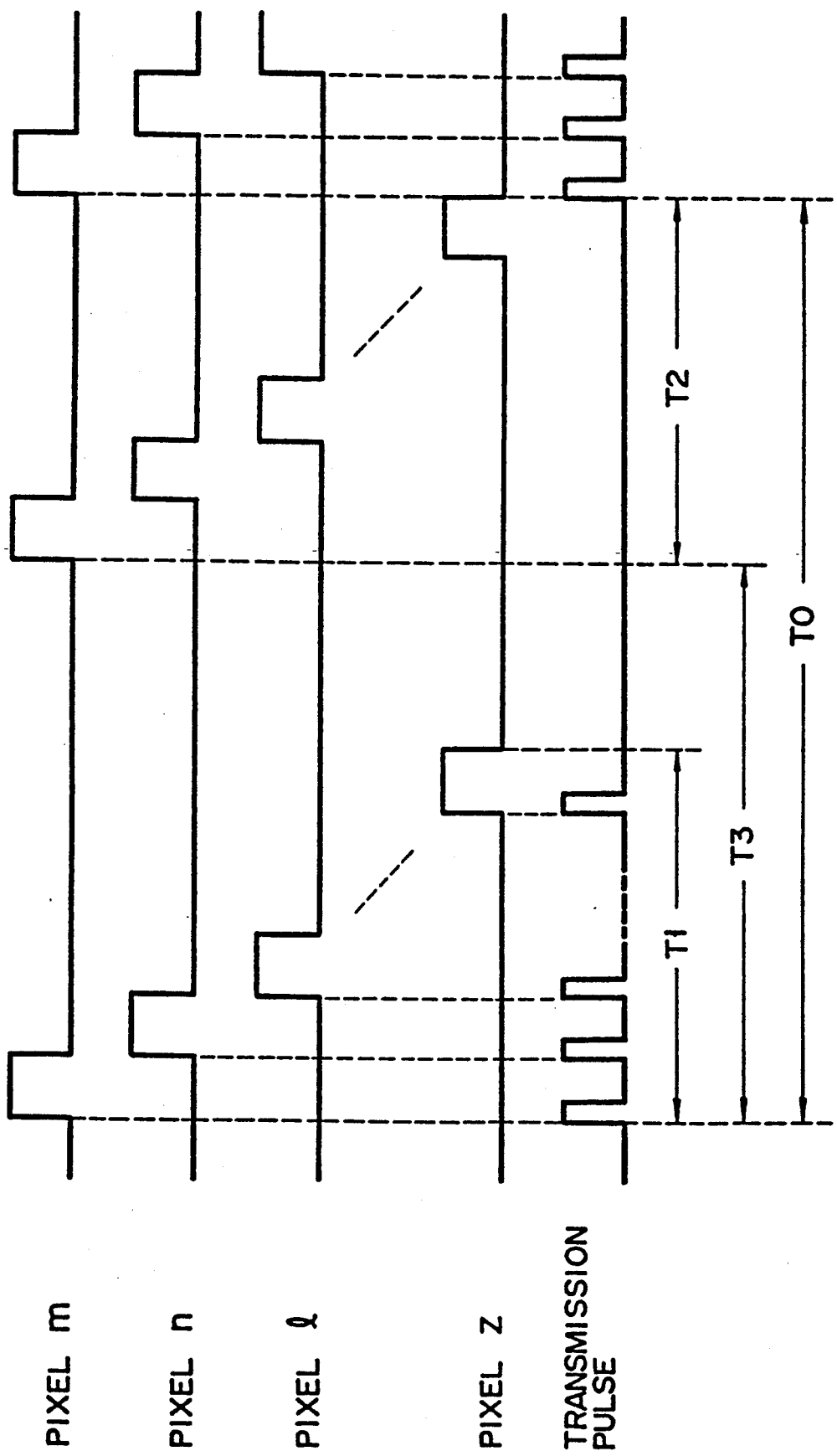
FIG. 13 is a signal waveform diagram illustrating the operation of the ultrasonic diagnosis apparatus according to the second embodiment.

FIG. 13 illustrates the relationship between beam transmission and reception timings of the individual pixels m, n, l, .... As illustrated, the period T0 for attaining an image signal for one line has a transmission period T1 and a reception period T2, and each pixel becomes ready for reception after a given period T3 from the transmission timing. This period T3 differs for each pixel. When the last pixel z for that scanning line completes its beam transmission and reception, multiplexer 9 selects the next signal electrode segment (scanning line), and the similar operation will be performed thereafter. In FIG. 13, the high durations of the signal waveforms are durations where the individual pixels are selected by multiplexers 8 and 9.

Since the difference T3 between the beam transmission and reception times corresponds to the distance between the slice 4 and the image pick-up element 6, the depth of the slice 4 from the skin of the target body 300 can be changed without stretching or compressing bellows 1 but simply by changing the reception timing T3. In this case, however, the resolution will be deteriorated so that a focusing mechanism or the like should desirably be provided.

With regard to image signal processing in diagnosis device 200, the second embodiment differs from the first embodiment only in gain control. In the second embodiment, gain control resistances are read out from frame memory 9 in synchronism with an image signal for each pixel being input to diagnosis device 200, whereby the image signal is gain-controlled for the position of each pixel.

As the second embodiment uses lens 5 for both the beam transmission and reception, it can provide a higher resolution than the first embodiment. The resolution in the slice is determined by the aperture angle of lens 5 and the frequency of an ultrasonic pulse as follows.

$$1.6 \, F/D\lambda \quad (\text{Here, 1.6 is about } \sqrt{2.4}.)$$

According to the second embodiment, as described above, an ultrasonic beam is irradiated on each pixel of a slice so as to scan the slice with the beam, the ultrasonic echo is converged on the image pick-up element using the ultrasonic lens so as to convert the sound pressure of the echo into an electric signal for each pixel, thereby providing a tomographic image. As compared with the conventional B-mode apparatuses, therefore, the second embodiment can provide an ultrasonic tomographic image with a improved resolution.

The second embodiment, as per the first embodiment, can have its system for reading an signal from the image pick-up element modified as shown in FIGS. 6 and 7 or can be itself modified, as shown in FIGS. 8 and 9, to eliminate a possible speckle pattern.

As explained above, according to this invention, an ultrasonic beam is irradiated on a target slice from a direction crossing the slice to sequentially scan the individual pixels of the slice, the ultrasonic echoes from the individuals are converted on the corresponding pixels of the ultrasonic image pick-up element through a lens, and these echoes are sequentially read out from the image pick-up element, thereby providing tomographic image information. Therefore, it is possible to provide an ultrasonic diagnosis apparatus which can acquire a tomographic image with improved azimuth resolution.

What is claimed is:

1. An ultrasonic diagnosis apparatus comprising:
   ultrasonic/electrical transducer means having a plurality of pixel electrodes arranged in a two-dimensional matrix, said pixel electrodes each corresponding to a given pixel, and being arranged facing a slice of a target body and parallel to said slice;
   an ultrasonic lens, arranged in parallel to said slice and to said transducer means, for converging an ultrasonic beam transmitted from each pixel electrode of said ultrasonic/electrical transducer means onto a corresponding point of said slice, and for converging an ultrasonic beam reflected at said points of said slice onto corresponding pixel electrodes of said ultrasonic/electrical transducer means;
   means for sequentially transmitting ultrasonic wave beams from said pixel electrodes of said ultrasonic-/electrical transducer means;
   signal readout means for sequentially reading out an electrical signal from said pixel electrodes of said ultrasonic/electrical transducer means which corresponds to an ultrasonic beam reflected at each of said points of said slice, after a predetermined time period after an operation of said transmission means; and
   imaging means for preparing image information of said slice from said electrical signal read out from said ultrasonic/electrical transducer means by said signal read out means.

2. An apparatus according to claim 1, wherein:
   said ultrasonic/electric transducer means comprises a group of ultrasonic/electric transducer elements arranged two-dimensionally in correspondence with each of said pixels of said slice; and
   said signal readout means comprises a first multiplexer for sequentially selecting rows of ultrasonic/electric transducer elements corresponding to each of a plurality of lines of said slice, and a second multiplexer for sequentially selecting said ultrasonic/electric transducer elements in one of said lines.

3. An apparatus according to claim 1, wherein said imaging means comprises two-dimensional gain control means for amplifying a signal from each of said pixels in accordance with a position of said each pixel in said slice.

4. An apparatus according to claim 1, wherein said signal readout means comprises means for changing said predetermined time period.

5. An apparatus according to claim 1, wherein:
   said ultrasonic/electrical transducer means comprises an electric/ultrasonic transducer element plate having opposite surfaces; a plurality of signal electrodes provided on one of said surfaces of said electric/ultrasonic transducer element plate with given pitches; and a plurality of ground electrodes provided with given pitches on the other of said surfaces of said electric/ultrasonic transducer element plate in a direction perpendicular to said signal electrodes; and
   said signal readout means comprises a first multiplexer coupled to said signal electrodes; and a second multiplexer coupled to said ground electrodes.

* * * * *